United States Patent
Baril et al.

(10) Patent No.: US 10,932,818 B2
(45) Date of Patent: Mar. 2, 2021

(54) REMOVABLE SEAL ASSEMBLY AND ACCESS SYSTEM INCLUDING THE SAME

(71) Applicant: COVIDIEN LP, Mansfield, MA (US)

(72) Inventors: Jacob C. Baril, Norwalk, CT (US); Saumya Banerjee, Hamden, CT (US); George S. Matta, Plainville, MA (US); Scott J. Prior, Shelton, CT (US); Christopher M. Meehan, New Haven, CT (US); Amy L. Kung, Hamden, CT (US)

(73) Assignee: Covidien LP, Mansfield, MA (US)

( * ) Notice: Subject to any disclaimer, the term of this patent is extended or adjusted under 35 U.S.C. 154(b) by 1 day.

(21) Appl. No.: 16/405,261

(22) Filed: May 7, 2019

(65) Prior Publication Data

US 2020/0352597 A1    Nov. 12, 2020

(51) Int. Cl.
*A61B 17/34* (2006.01)
*A61B 17/00* (2006.01)
*A61B 17/02* (2006.01)

(52) U.S. Cl.
CPC .. *A61B 17/3423* (2013.01); *A61B 2017/3419* (2013.01); *A61B 2017/3464* (2013.01)

(58) Field of Classification Search
CPC ............ A61B 17/3462; A61B 17/3423; A61B 17/3439; A61B 17/3498; A61B 17/3417; A61B 17/0293; A61B 17/0206; A61B 17/3421; A61B 17/3431; A61B 2017/3419; A61B 2017/3464; A61B 2017/3482; A61B 2017/3466; A61B 2017/347; A61B 2017/3449; A61B 2017/00557; A61B 2017/3429; A61B 2017/0225; A61B 2017/3488; A61B 2017/3492; A61B 2017/00265
USPC ......................................... 600/201–245, 184
See application file for complete search history.

(56) References Cited

U.S. PATENT DOCUMENTS

| | | | |
|---|---|---|---|
| 6,942,671 B1 * | 9/2005 | Smith ................ | A61B 17/3462 606/108 |
| 7,323,004 B2 * | 1/2008 | Parihar .............. | A61B 17/0057 128/898 |
| 7,883,461 B2 | 2/2011 | Albrecht et al. | |
| 7,922,656 B2 | 4/2011 | Beckman et al. | |

(Continued)

OTHER PUBLICATIONS

Extended European Search Report issued in corresponding Appl. No. EP 20172803.7 dated Sep. 11, 2020 (7 pages).

*Primary Examiner* — Pedro Philogene
(74) *Attorney, Agent, or Firm* — Carter, DeLuca & Farrell LLP

(57) ABSTRACT

A removable seal assembly configured to engage an access device includes a body including a proximal portion, a distal portion, and a passageway extending longitudinally therethrough. The proximal portion defines an annular distally-oriented surface and the distal portion defines an annular proximally-oriented surface. The body is configured for positioning within an access device such that the annular distally-oriented surface and the annular proximally-oriented surface engage opposing surfaces of the access device therebetween. An O-ring disposed about the body between the annular distally-oriented surface and the annular proximally-oriented surface. The O-ring is configured to establish a fluid tight-seal between the body and the access device.

13 Claims, 3 Drawing Sheets

(56) References Cited

U.S. PATENT DOCUMENTS

| | | | |
|---|---|---|---|
| 8,109,873 B2 | 2/2012 | Albrecht et al. | |
| 8,419,635 B2* | 4/2013 | Shelton, IV | A61B 17/3423 |
| | | | 600/208 |
| 9,737,334 B2* | 8/2017 | Huey | A61B 17/3423 |
| 10,076,358 B2* | 9/2018 | Zergiebel | A61M 13/003 |
| 2005/0020884 A1* | 1/2005 | Hart | A61B 17/0293 |
| | | | 600/206 |
| 2007/0055107 A1 | 3/2007 | Wenchell | |
| 2008/0249475 A1* | 10/2008 | Albrecht | A61B 17/3498 |
| | | | 604/167.06 |
| 2009/0187079 A1 | 7/2009 | Albrecht et al. | |
| 2010/0204548 A1 | 8/2010 | Bonadio et al. | |
| 2013/0012782 A1 | 1/2013 | Stearns et al. | |
| 2016/0100857 A1 | 4/2016 | Wachli et al. | |

* cited by examiner

REMOVABLE SEAL ASSEMBLY AND ACCESS SYSTEM INCLUDING THE SAME

FIELD

The present disclosure relates to tissue specimen removal and, more particularly, to a removable seal assembly and access system including the same to facilitate removal of a tissue specimen from an internal body cavity.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a removable seal assembly configured to engage an access device. The removable seal assembly includes a body including a proximal portion, a distal portion, and a passageway extending longitudinally therethrough. The proximal portion defines an annular distally-oriented surface and the distal portion defines an annular proximally-oriented surface. The annular distally-oriented surface and the annular proximally-oriented surface are longitudinally spaced-apart to define a longitudinal length therebetween. The body is configured for positioning within an access device such that the annular distally-oriented surface and the annular proximally-oriented surface engage opposing surfaces of the access device therebetween. An O-ring is disposed about the body between the annular distally-oriented surface and the annular proximally-oriented surface. The O-ring is configured to establish a fluid tight-seal between the body and the access device.

In an aspect of the present disclosure, an instrument seal disposed within the passageway. The instrument seal is configured to establish a fluid-tight seal about an instrument inserted through the passageway.

In another aspect of the present disclosure, a zero seal is disposed within the passageway. The zero seal is configured to establish a fluid-tight seal in the absence of an instrument inserted through the passageway. The zero seal may be formed from a plurality of zero seal components stacked on top of one another.

In still another aspect of the present disclosure, the proximal portion of the body defines a conical-shaped configuration including an apex proximal end and a base distal end.

In yet another aspect of the present disclosure, the distal portion of the body includes a plurality of circumferentially spaced-apart feet. Each foot defines a portion of the annular proximally-oriented surface such that the annular proximally-oriented surface is discontinuous. Each foot may be resiliently flexible.

In still yet another aspect of the present disclosure, the removable seal assembly further includes at least one seal component and a cap configured to retain the at least one seal component in engagement with the body.

An access system provided in accordance with aspects of the present disclosure includes an access device and a removable seal assembly. The access device is configured for positioning in an opening in tissue and includes a first body defining a first passageway therethrough, a first annular proximally-oriented surface towards a proximal end thereof, and a first annular distally-oriented surface towards a distal end thereof. The removable seal assembly is configured for releasable engagement within the first passageway of the access device and includes a second body including a proximal portion, a distal portion, and a second passageway extending longitudinally therethrough. The proximal portion defines a second annular distally-oriented surface and the distal portion defines a second annular proximally-oriented surface. The second body is configured for positioning within the first passageway of the first body such that the second annular distally-oriented surface is engaged with the first annular proximally-oriented surface and such that the second annular proximally-oriented surface is engaged with the first annular distally-oriented surface. The removable seal assembly further includes an O-ring disposed about the second body between the second annular distally-oriented surface and the second annular proximally-oriented surface. The O-ring is configured to establish a fluid tight-seal between the first and second bodies.

In an aspect of the present disclosure, the access device is a tissue retractor.

In another aspect of the present disclosure, the removable seal assembly further includes an instrument seal disposed within the second passageway and configured to establish a fluid-tight seal about an instrument inserted through the second passageway.

In still another aspect of the present disclosure, the removable seal assembly further includes a zero seal disposed within the second passageway and configured to establish a fluid-tight seal in the absence of an instrument inserted through the second passageway. The zero seal may be formed from a plurality of zero seal components stacked on top of one another.

In yet another aspect of the present disclosure, the distal portion of the second body includes a plurality of circumferentially spaced-apart feet. Each foot defines a portion of the annular proximally-oriented surface such that the annular proximally-oriented surface is discontinuous.

In still yet another aspect of the present disclosure, each foot is resiliently flexible and configured to snap into engagement with the access device.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

The present disclosure provides a removable seal assembly and access system including the removable seal assembly and a tissue retractor to facilitate removal of a tissue specimen from an internal body cavity. Although detailed for use with a tissue retractor, the removable seal assembly of the present disclosure may be utilized with other access components such as, for example, other tissue retractors, tissue guards, etc.

Figure 1:
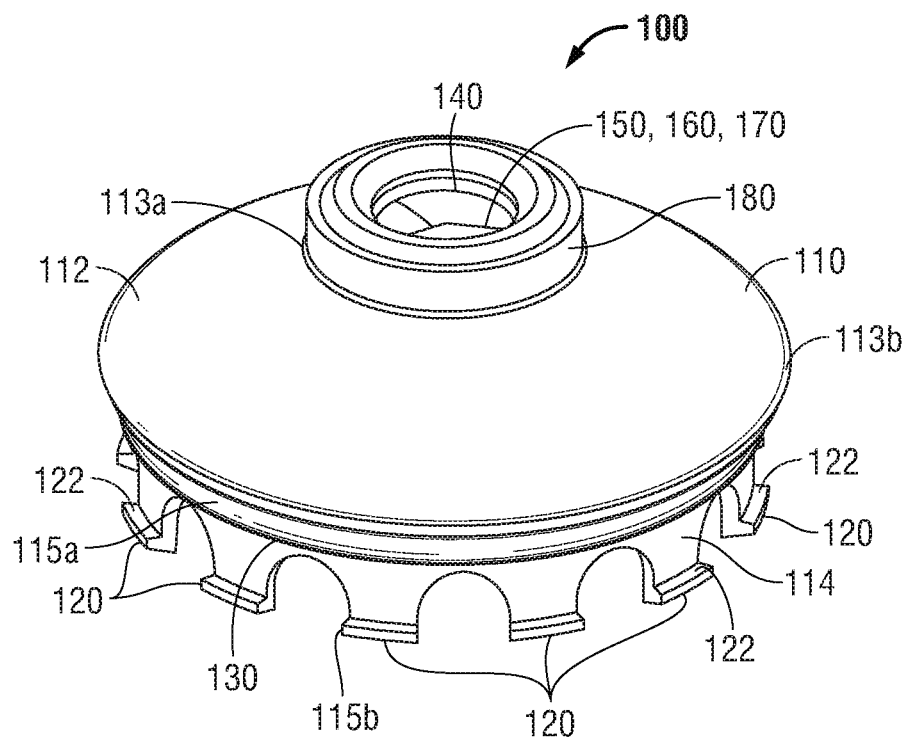
FIG. 1 is a top, perspective view of a removable seal assembly provided in accordance with the present disclosure.
Figure 2:
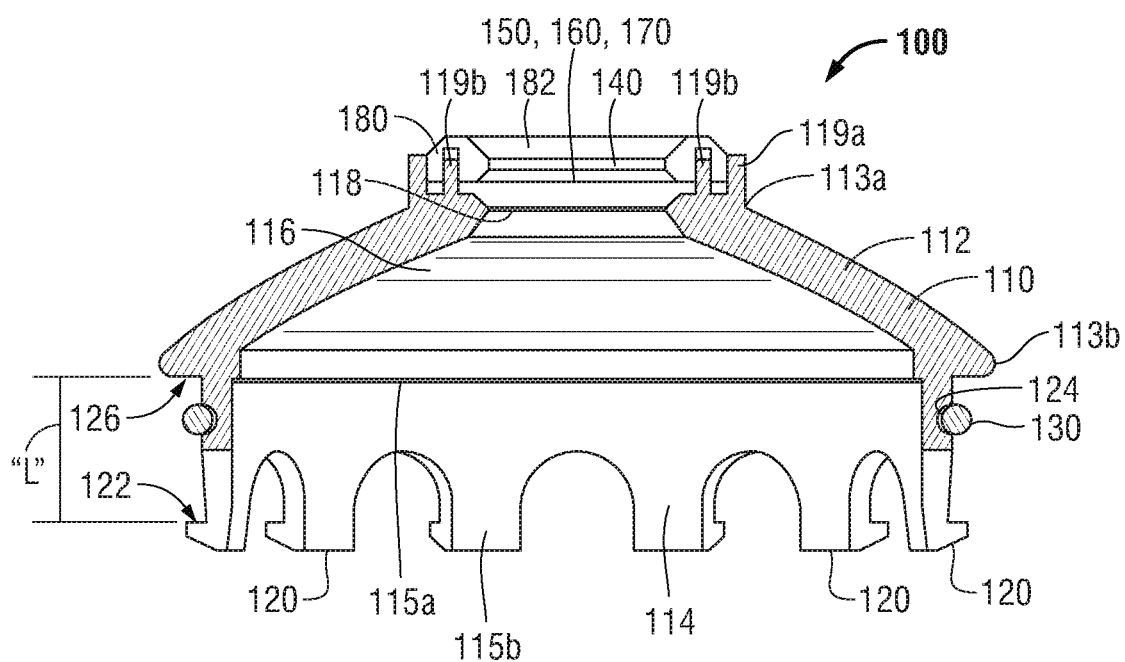
FIG. 2 is a transverse, cross-sectional view of the removable seal assembly of FIG. 1.
Figure 3:
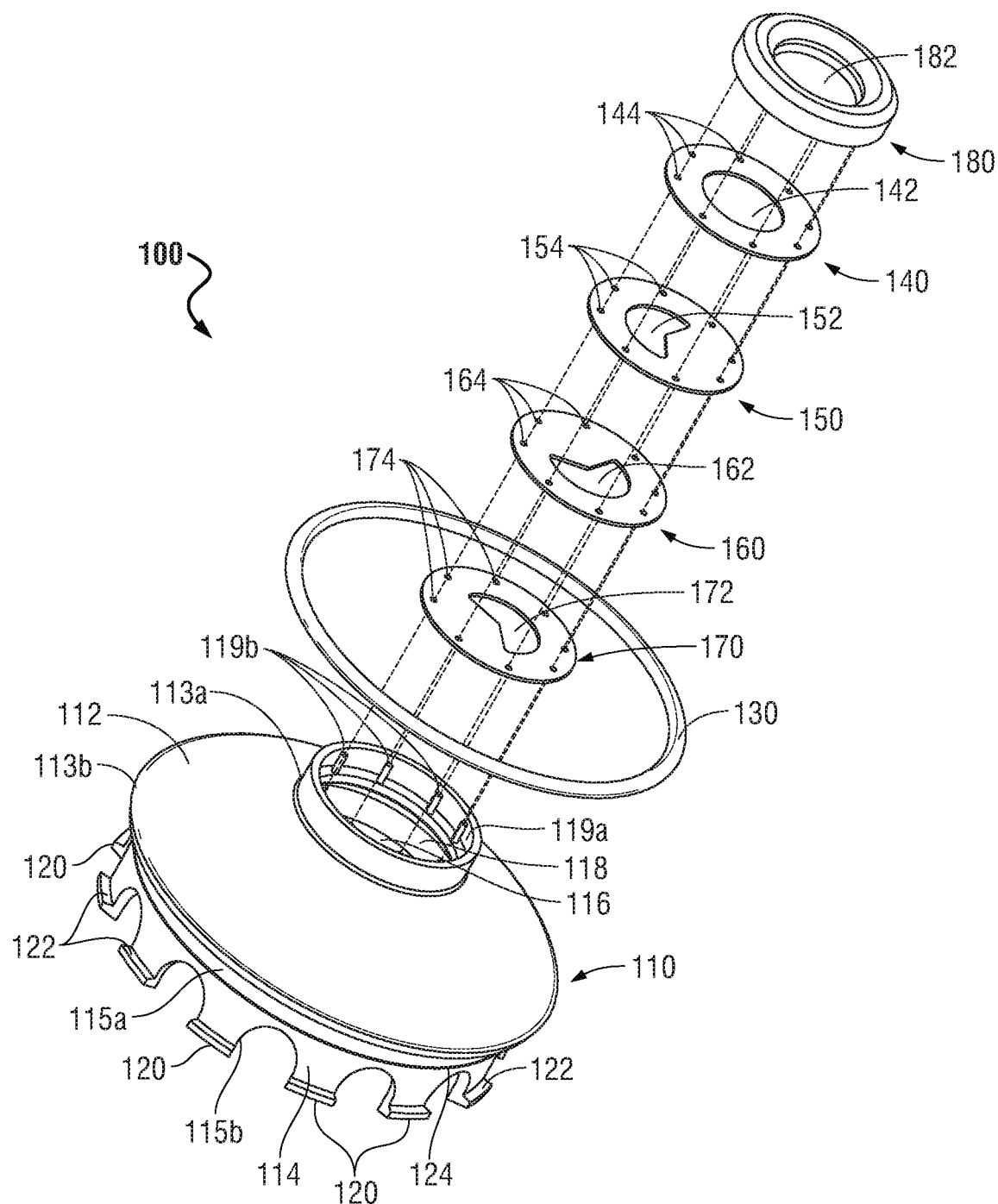
FIG. 3 is an exploded, perspective view of the removable seal assembly of FIG. 1.

Turning to FIGS. 1-3, a removable seal assembly provided in accordance with the present disclosure is shown generally identified by reference numeral 100. Removable seal assembly 100 includes a body 110 having a proximal portion 112 and a distal portion 114 and defining a passageway 116 extending longitudinally therethrough. Body 110 may be formed from a suitable plastic via injection molding, although other suitable materials and/or manufacturing methods are also contemplated.

Proximal portion 112 of body 110 has a conical-shaped configuration and defines an aperture 118 therethrough at apex end 113a thereof that is disposed in communication with passageway 116. In embodiments, aperture 118 defines a diameter of at least 20 mm. Proximal portion 112 of body 110 further includes a collar 119a disposed about aperture 118 at apex end 113a thereof and including a plurality of posts 119b spaced circumferentially about aperture 118 and extending proximally from collar 119a. Proximal portion 112 of body 110 additionally defines an open base end 113b that, due to the conical-shaped configuration of body 110, defines a diameter greater than that of aperture 118.

Distal portion 114 of body 110 defines a tubular configuration and extends distally from open base end 113b of proximal portion 112 of body 110. Distal portion 114 defines open proximal and distal ends 115a, 115b, respectively. Open proximal end 115a communicates with open base end 113b of proximal portion 112. In this manner, passageway 116 is defined longitudinally from apex end 113a of open proximal portion 112 of body 110 through open distal end 115b of distal portion 114 of body 110.

Distal portion 114 of body 110 defines a plurality of spaced-apart feet 120 extending outwardly from open distal end 115b thereof. Each foot 120 is resiliently flexible and defines a proximally-oriented surface 122. The proximally-oriented surfaces 122 cooperate to define a discontinuous proximally-oriented annular surface extending about open distal end 115b of distal portion 114 of body 110. Distal portion 114 of body 110 further defines a recess 124 defining a semi-circular cross-sectional configuration (although other configurations are also contemplated) and extending annularly about an exterior of distal portion 114 of body 110.

An outer diameter of proximal portion 112 at open base end 113b thereof is greater than an outer diameter of distal portion 114 of body 110 at open proximal end 115a thereof such that open base end 113b of proximal portion 112 overhangs open proximal end 115a of distal portion 114 to define a distally-oriented surface 126 extending annularly about open base end 113b of proximal portion 112 of body 110. Distally-oriented surface 126 and the discontinuous proximally-oriented annular surface defined by proximally-oriented surfaces 122 define a longitudinal length "L" (FIG. 2) therebetween. As detailed below, distally-oriented surface 126 is configured to engage a proximally-oriented surface 322 of a tissue retractor 300 or other suitable access device while proximally-oriented surfaces 122 are configured to engage a distally-oriented surface 324 of a tissue retractor 300 or other suitable access device to releasably engage removable seal assembly 100 therewith (see FIG. 4). Depending upon the tissue retractor 300 (FIG. 4) or suitable access device that removable seal assembly 100 is configured for use with, the length "L" may vary.

Continuing with reference to FIGS. 1-3, removable seal assembly 100 further includes an elastomeric O-ring 130 configured for partial receipt within recess 124 of distal portion 114 of body 110, e.g., with a portion of O-ring 130 seated within recess 124 to inhibit longitudinal movement of O-ring 130 about body 110 and a portion of O-ring 130 extending radially outwardly from recess 124. With O-ring 130 positioned within recess 124, O-ring 130 is disposed along the longitudinal length "L" (FIG. 2), e.g., between distally-oriented surface 126 and the discontinuous proximally-oriented annular surface defined by proximally-oriented surfaces 122. As detailed below, O-ring 130 is configured to engage an annular inwardly-oriented surface 326 of a tissue retractor 300 or other suitable access device to establish a fluid-tight seal between removable seal assembly 100 and the tissue retractor 300 (FIG. 4) or other suitable access device.

Removable seal assembly 100 also includes an instrument seal 140 and a plurality of zero seal components 150, 160, 170 cooperating to define a zero seal. Instrument seal 140 is formed from a flexible material and defines a central aperture 142 configured to receive a surgical instrument therethrough and to establish a fluid-tight seal about the outer diameter of the surgical instrument. Instrument seal 140 further includes mounting holes 144 defined therethrough and spaced-apart circumferentially about the perimeter thereof.

Zero seal components 150, 160, 170 are each formed from a flexible material and define non-circular cut-outs 152, 162, 172. Zero seal components 150, 160, 170 may be identical to one another but disposed in different rotational orientations such that the non-circular cut-outs 152, 162, 172 are at least partially-misaligned with one another to establish a fluid-tight seal therebetween when zero seal components 150, 160, 170 are stacked on top of one another. Despite establishing a fluid-tight seal in the absence of a surgical instrument, zero seal components 150, 160, 170 are also capable of flexible to accommodate a surgical instrument therethrough. Each zero seal component 150, 160, 170 further includes mounting holes 154, 164, 174 defined therethrough and spaced-apart circumferentially about the perimeter thereof.

Zero seal components 150, 160, 170 are configured for engagement with collar 119a, e.g., via receipt of posts 119b through mounting holes 154, 164, 174 such that zero seal components 150, 160, 170 extend across and form a fluid-tight seal across aperture 118. Instrument seal 140 is likewise configured for engagement with collar 119a, e.g., via receipt of posts 119b through mounting holes 144, proximally of zero seal components 150, 160, 170. However, other suitable configurations for engaging instrument seal 140 and/or zero seal components 150, 160, 170 with collar 119a are also contemplated.

Removable seal assembly 100 further includes a cap 180 defining a center opening 182 extending therethrough. Cap 180 is configured for positioning about collar 119a of proximal portion 112 of body 110 to retain instrument seal 140 and zero seal components 150, 160, 170 in engagement with collar 119a. Cap 180 may be welded, adhered, snap-fit, or otherwise engaged about collar 119a. Center opening 182 of cap 180 is aligned with and defines a diameter similar to aperture 118 of proximal portion 112 of body 110.

Figure 4:
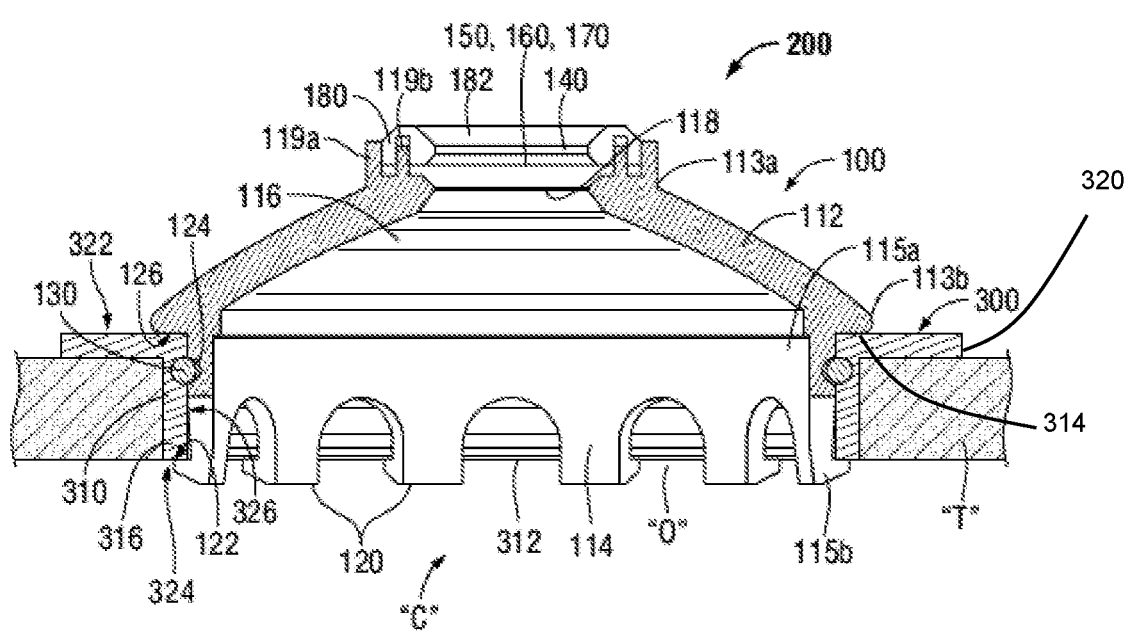
FIG. 4 is a transverse, cross-sectional view of an access system provided in accordance with the present disclosure engaged within an opening in tissue and including the removable seal assembly of FIG. 1 and a tissue retractor.

Turning to FIG. 4, an access system 200 provided in accordance with the present disclosure is shown in use within an opening "O" in tissue "T." Access system 200 includes removable seal assembly 100 and a tissue retractor 300 or other suitable access device.

Tissue retractor 300 is configured for positioning with within an opening "O" in tissue "T" to at least maintain opening "O," if not to retract tissue "T" to enlarge opening "O." Tissue retractor 300 includes a body 310 define a passageway 312 extending longitudinally therethrough. Tissue retractor 300 further includes a proximal flange 320 extending radially-outwardly from a proximal end 314 of body 310. Proximal flange 320 defines a proximally-oriented surface 322. Body 310 further defines a distally-oriented surface 324 disposed at distal end 316 of body 310. Proximally-oriented surface 322 and distally-oriented surface 324 define a longitudinal length therebetween that approximates the longitudinal length "L" to enable operable engagement of removable seal assembly 100 with tissue retractor 300, as detailed below. Passageway 312 of body 310 of tissue retractor 300 is surrounded, e.g., defined, by an annular inwardly-oriented surface 326 of body 310.

In use, with tissue retractor 300 positioned within the opening "O" in tissue "T," removable seal assembly 100, lead by distal portion 114 of body 110 of removable seal assembly 100, is inserted through passageway 312 of body 310 of tissue retractor 300, whereby feet 120 of removable seal assembly 100 may be deflected radially inwardly to accommodate this insertion of removable seal assembly 100. Body 110 of removable seal assembly 100 is inserted through passageway 312 of body 310 of tissue retractor 300 until feet 120 pass distally beyond distal end 316 of body 310, thus enabling feet 120 to return under bias from the deflected positions thereof to at-rest positions thereof, wherein proximally-oriented surfaces 122 of feet 120 engage, e.g., snap-into engagement with, distally-oriented surface 324 of tissue retractor 300. Simultaneously or near in time to the engagement of proximally-oriented surfaces 122 of feet 120 with distally-oriented surface 324 of tissue retractor 300, distally-oriented surface 126 of proximal portion 112 of body 110 of removable seal assembly 100 engages proximally-oriented surface 322 of tissue retractor 300. These engagements releasably secure removable seal assembly 100 within tissue retractor 300. Further, upon this engagement, O-ring 130 is at least partially compressed into annular inwardly-oriented surface 326 of tissue retractor 300 to establish a fluid-tight seal between removable seal assembly 100 and tissue retractor 300.

Continuing with reference to FIG. 4, with removable seal assembly 100 engaged within tissue retractor 300 as detailed above, insufflation of an internal body cavity "C" may be achieved and maintained both in the absence of a surgical instrument passing through system 200 and with a surgical instrument passing through system 200. When maintenance of insufflation is no longer required, removable seal assembly 100 may be disengaged and removed from tissue retractor 300 while tissue retractor 300 remains in position within the opening "O" in tissue "T."Alternatively, system 200 may be entirely removed from the opening "O" in tissue "T." Likewise, instead of engaging removable seal assembly 100 with tissue retractor 300 after tissue retractor 300 has already been positioned within the opening "O" in tissue "T," removable seal assembly 100 may be engaged with tissue retractor 300 prior thereto such that system 200 may be entirely positioned within the opening "O" in tissue "T."

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A removable seal assembly configured to engage an access device, the removable seal assembly comprising:
   a body including a proximal portion, a distal portion, and a passageway extending longitudinally therethrough, wherein the proximal portion defines an annular distally-oriented surface and wherein the distal portion includes a discontinuous annular proximally-oriented surface defined by a plurality of circumferentially spaced-apart feet, the annular distally-oriented surface and the discontinuous annular proximally-oriented surface longitudinally spaced-apart to define a longitudinal length therebetween, wherein the body is configured for positioning within an access device such that the annular distally-oriented surface and the discontinuous annular proximally-oriented surface engage opposing surfaces of the access device therebetween, the plurality of circumferentially spaced apart feet configured to contact a side surface of the access device; and
   an O-ring disposed about the body between the annular distally-oriented surface and the discontinuous annular proximally-oriented surface, the O-ring configured to establish a fluid tight-seal between the body and the access device.

2. The removable seal assembly according to claim 1, further comprising an instrument seal disposed within the passageway, the instrument seal configured to establish a fluid-tight seal about an instrument inserted through the passageway.

3. The removable seal assembly according to claim 1, further comprising a zero seal disposed within the passageway, the zero seal configured to establish a fluid-tight seal in the absence of an instrument inserted through the passageway.

4. The removable seal assembly according to claim 3, wherein the zero seal is formed from a plurality of zero seal components stacked on top of one another.

5. The removable seal assembly according to claim 1, wherein the proximal portion of the body defines a conical-shaped configuration including an apex proximal end and a base distal end.

6. The removable seal assembly according to claim 1, wherein each foot of the plurality of circumferentially spaced-apart feet is resiliently flexible.

7. The removable seal assembly according to claim 1, further comprising:
at least one seal component; and
a cap configured to retain the at least one seal component in engagement with the body.

8. An access system, comprising:
an access device configured for positioning in an opening in tissue, the access device including a first body defining a first passageway therethrough, a first annular proximally-oriented surface towards a proximal end thereof, and a first annular distally-oriented surface towards a distal end thereof; and
a removable seal assembly configured for releasable engagement within the first passageway of the access device, the removable seal assembly including:
a second body including a proximal portion, a distal portion, and a second passageway extending longitudinally therethrough, wherein the proximal portion defines a second annular distally-oriented surface and wherein the distal portion includes a second discontinuous annular proximally-oriented surface defined by a plurality of circumferentially spaced-apart feet, the plurality of circumferentially spaced apart feet configured to contact a side surface of the access device, wherein the second body is configured for positioning within the first passageway of the first body such that the second annular distally-oriented surface is engaged with the first annular proximally-oriented surface and such that a portion of the second discontinuous annular proximally-oriented surface is engaged with the first annular distally-oriented surface; and
an O-ring disposed about the second body between the second annular distally-oriented surface and the second discontinuous annular proximally-oriented surface, the O-ring configured to establish a fluid tight-seal between the first and second bodies.

9. The access system according to claim 8, wherein the access device is a tissue retractor.

10. The access system according to claim 8, wherein the removable seal assembly further comprises an instrument seal disposed within the second passageway, the instrument seal configured to establish a fluid-tight seal about an instrument inserted through the second passageway.

11. The access system according to claim 8, further comprising a zero seal disposed within the second passageway, the zero seal configured to establish a fluid-tight seal in the absence of an instrument inserted through the second passageway.

12. The access system according to claim 11, wherein the zero seal is formed from a plurality of zero seal components stacked on top of one another.

13. The access system according to claim 8, wherein each foot of the plurality of circumferentially spaced-apart feet is resiliently flexible and configured to snap into engagement with the access device.

* * * * *